US008320981B1

(12) United States Patent
Mayer et al.

(10) Patent No.: US 8,320,981 B1
(45) Date of Patent: Nov. 27, 2012

(54) ENHANCED OPTICAL SENSOR MODULE

(75) Inventors: Carl Mayer, Overland Park, KS (US); Craig Seyl, Olathe, KS (US); Joseph Lee Hollmann, Kansas City, MO (US); Eric Weiss, Sunnyvale, CA (US); Lyle Frank Weaver, Woodside, CA (US); Timothy A. Fayram, Gilroy, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1496 days.

(21) Appl. No.: 11/771,547

(22) Filed: Jun. 29, 2007

(51) Int. Cl.
*A61B 5/1455* (2006.01)

(52) U.S. Cl. ........ 600/310; 600/322; 600/323; 600/326; 600/320

(58) Field of Classification Search .................. 600/310, 600/322–328, 333, 339, 342, 316
See application file for complete search history.

(56) References Cited

U.S. PATENT DOCUMENTS

| | | | |
|---|---|---|---|
| 3,847,483 A | 11/1974 | Shaw et al. | |
| 4,114,604 A | 9/1978 | Shaw et al. | |
| 5,040,533 A | 8/1991 | Fearnot | |
| 5,139,025 A | 8/1992 | Lewis et al. | |
| 5,553,615 A | 9/1996 | Carim et al. | |
| 5,638,816 A * | 6/1997 | Kiani-Azarbayjany et al. | 600/316 |
| 5,720,284 A * | 2/1998 | Aoyagi et al. | 600/322 |
| 5,842,979 A | 12/1998 | Jarman | |
| 5,902,235 A | 5/1999 | Lewis et al. | |
| 5,902,326 A | 5/1999 | Lessar et al. | |
| 5,931,779 A | 8/1999 | Arakaki et al. | |
| 6,061,583 A | 5/2000 | Ishihara et al. | |
| 6,125,290 A * | 9/2000 | Miesel | 600/325 |
| 6,216,021 B1 | 4/2001 | Franceschini et al. | |
| 6,246,894 B1 * | 6/2001 | Steuer et al. | 600/322 |
| 6,330,464 B1 | 12/2001 | Colvin et al. | |
| 6,409,675 B1 | 6/2002 | Turcott | |
| 6,587,701 B1 * | 7/2003 | Stranc et al. | 600/310 |
| 6,606,509 B2 | 8/2003 | Schmitt | |
| 6,662,031 B1 | 12/2003 | Khalil | |
| 6,731,967 B1 | 5/2004 | Turcott | |
| 6,931,272 B2 | 8/2005 | Burnes | |
| 2002/0016534 A1 * | 2/2002 | Trepagnier et al. | 600/316 |
| 2002/0058865 A1 | 5/2002 | Cheng et al. | |
| 2004/0220629 A1 | 11/2004 | Kamath et al. | |
| 2005/0070778 A1 * | 3/2005 | Lackey et al. | 600/366 |
| 2006/0063995 A1 * | 3/2006 | Yodh et al. | 600/323 |

* cited by examiner

*Primary Examiner* — Eric Winakur
*Assistant Examiner* — Chu Chuan (JJ) Liu
(74) *Attorney, Agent, or Firm* — Steven M. Mitchell

(57) ABSTRACT

An implantable system includes light sources to transmit toward vascularized tissue, in a time multiplexed manner, light having a first wavelength of approximately 660 nm, light having a second wavelength of approximately 810 nm, light having a third wavelength of approximately 910 nm, and light having a fourth wavelength of approximately 980 nm. The system includes one or more light detector to detect light of the first, second, third and fourth wavelengths scattered by vascularized tissue. Additionally, one or more processor is configured to determine levels of blood oxygen saturation based on the detected scattered light of the first and third wavelengths, determine levels of tissue oxygen saturation based on the detected scattered light of the first and third wavelengths, determine levels of hemoglobin concentration based on the detected scattered light of the second wavelength, and determine levels of tissue hydration based on the detected scattered light of the second and fourth wavelengths.

19 Claims, 8 Drawing Sheets

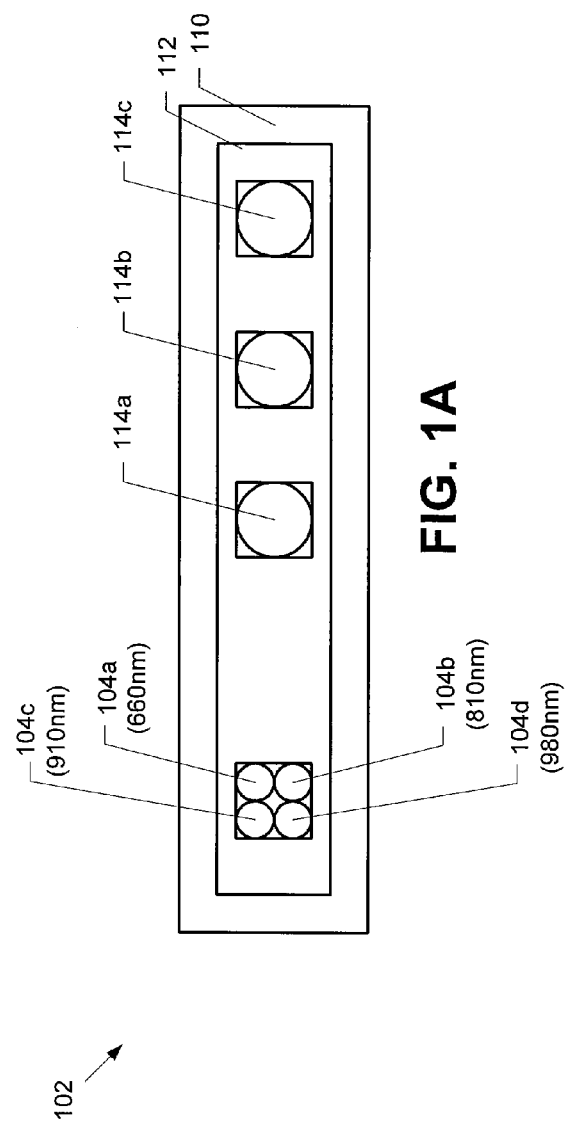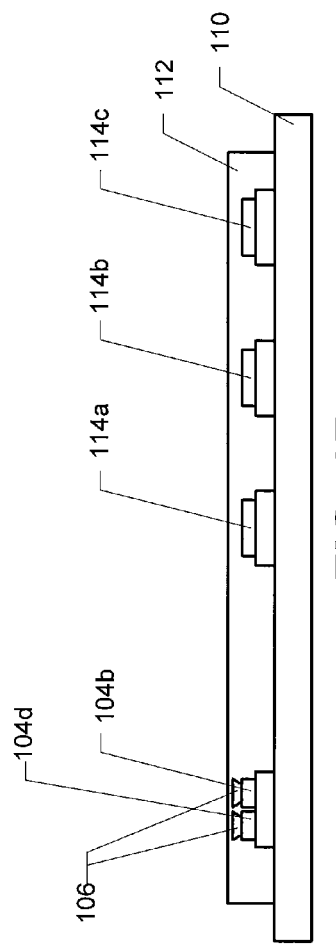

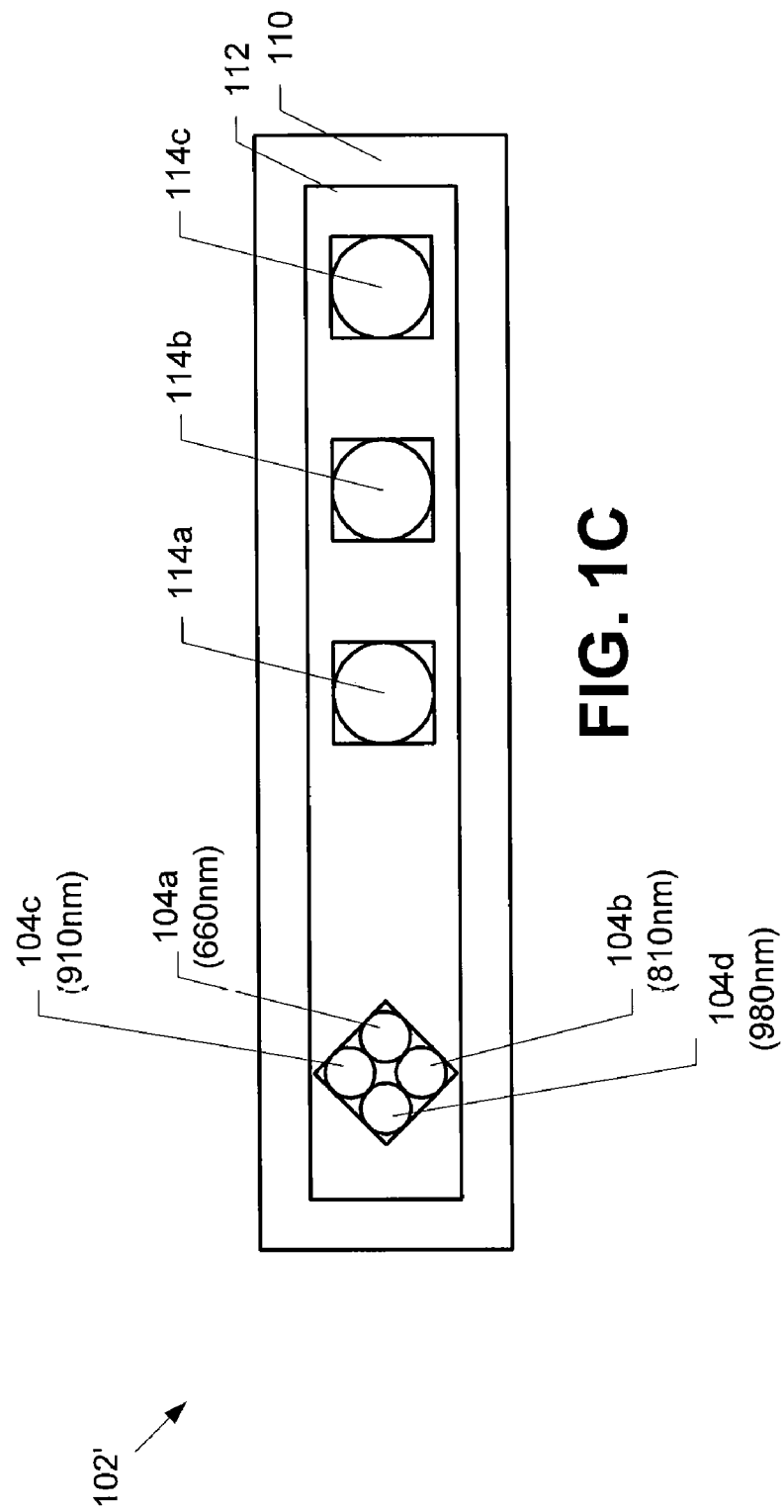

ENHANCED OPTICAL SENSOR MODULE

CROSS REFERENCE TO RELATED APPLICATION

The present invention relates to the following commonly assigned applications, each of which is incorporated herein by reference: U.S. patent application Ser. No. 10/913,942, entitled "Autonomous Sensor Modules for Patient Monitoring", filed Aug. 5, 2004; U.S. patent application Ser. No. 11/282,198, entitled "Implantable Self-Calibrating Optical Sensors," filed Nov. 17, 2005; and U.S. patent application Ser. No. 11/231,555, entitled "Implantable Multi-Wavelength Oximeter Sensor," filed Sep. 20, 2005.

FIELD OF THE INVENTION

Embodiments of the present invention relate to implantable optical sensors that are used, e.g., for obtaining measures of blood oxygen saturation, tissue oxygen saturation, hemoglobin concentration and/or tissue hydration.

BACKGROUND

Blood oxygen saturation is the relative amount of oxygenated hemoglobin in all of the hemoglobin present in the blood stream. This hemoglobin is packaged in biconcave discs of approximately 10 micrometers diameter which commonly occur with a density of approximately five million red blood cells per cubic millimeter. When radiant energy (e.g., light) is incident upon red blood cells, the red blood cells both scatter and transmit the incident radiant energy. The differential absorption by oxygenated hemoglobin (also known as oxyhemoglobin) and deoxygenated hemoglobin (also known as deoxyhemoglobin) of the radiant energy reflected by and transmitted through the red blood cells furnishes the basis for oxygen saturation measurements.

More specifically, pulse oximeters use light of two or more different centered wavelengths (e.g., produced by two or more light sources) to obtain measures of blood oxygen saturation by measuring the absorption and/or scattering of oxyhemoglobin and deoxyhemoglobin. The measured scattering data allows for the calculation of the relative concentrations of reduced hemoglobin (Hb) and oxyhemoglobin (HbO), and therefore blood oxygen saturation levels, since the scattering relationships are known.

While implantable pulse oximetry type oxygen saturation sensors have been proposed, it would be beneficial if such sensors can be used to measure more than just oxygen saturation. Further, it would be beneficial to increase the accuracy of such sensors.

SUMMARY

Embodiments of the present invention are directed to implantable systems, and methods for use therewith. In accordance with an embodiment, an implantable system includes a plurality of light sources to transmit toward vascularized tissue, in a time multiplexed manner, light having a first wavelength of approximately 660 nm, light having a second wavelength of approximately 810 nm, light having a third wavelength of approximately 910 nm, and light having a fourth wavelength of approximately 980 nm. The system includes one or more light detector to detect light of the first, second, third and fourth wavelengths scattered by the vascularized tissue. Additionally, the system includes one or more processor configured to determine levels of blood oxygen saturation based on the detected scattered light of the first and third wavelengths ($\approx$660 nm and 910 nm), determine levels of tissue oxygen saturation based on the detected scattered light of the first and third wavelengths ($\approx$660 nm and 910 nm), determine levels of hemoglobin concentration based on the detected scattered light of the second wavelength ($\approx$810 nm), and determine levels of tissue hydration based on the detected scattered light of the second and fourth wavelength ($\approx$810 nm and 910 nm).

In accordance with specific embodiments, the one or more light detector is one or more Silicon photodetector.

In accordance with specific embodiments, hemoglobin concentration is determined using the following equation:

$$[H] = \frac{\ln\left(\frac{I(810)}{I_0(810)}\right)}{k_{HbO}^{810} S_{tO2} + k_{Hb}^{810}(1 - S_{tO2})},$$

where [H] is the hemoglobin concentration, $k_{HbO}^{810}$ is a known molar absorption coefficient of oxygenated hemoglobin (HbO) for the light having a wavelength of approximately 810 nm, $k_{Hb O}^{810}$ is a known molar absorption coefficient of deoxygenated hemoglobin (Hb) for the light having a wavelength of approximately 810 nm, $S_{tO2}$ is the level of tissue oxygen saturation determined by the system, $I_0(810)$ is an initial intensity of the light having a wavelength of approximately 810 nm, and $I(810)$ is an intensity of the light having a wavelength of approximately 810 nm as detected by the one or more light detector.

In accordance with specific embodiments, the system includes an analog to digital converter (A/D) that converts intensities of light detected by the one or more light detector to digital values. In such embodiments, a value indicative of an initial tissue hydration level can be determining using the following equation:

$$W_0 = \frac{\ln(\text{counts}(980)) - \left(k_{HbO}\left(\frac{S_{tO2}}{100}\right) + k_{Hb}\left(1 - \frac{S_{tO2}}{100}\right)\right)[H]}{\mu_{a\_w}^{980}},$$

where $W_0$ is the value indicative of the initial tissue hydration level, counts(980) is a digital value provided using the A/D that is indicative of an intensity of the light of having a wavelength of approximately 980 nm detected by the one or more light detector, and $\mu_{a\_w}^{980}$, is the known absorption coefficient of water for the light having a wavelength of approximately 980 nm.

In accordance with specific embodiments, a value indicative of a change in tissue hydration is determined using the following equation:

$$\Delta W = W_0 - \frac{\ln(\text{counts}(980)) + \left(k_{Hbo}\left(\frac{S_{tO2}}{100}\right) + k_{Hb}\left(1 - \frac{S_{tO2}}{100}\right)\right)[H]}{\mu_{a\_w}^{980}},$$

where $\Delta W$ is the value indicative of the change in tissue hydration.

In accordance with specific embodiment, pulmonary edema can be monitored for based on the levels of tissue hydration determined by the system. In such embodiments, an alert can be triggered when a change in tissue hydration exceeds a corresponding threshold.

In accordance with specific embodiments, levels of oxygenated hemoglobin (HbO) and deoxygenated hemoglobin (Hb) can be determined based on the detected scattered light of the first and third wavelengths. In such embodiments, ademia can be detected and/or tracked using determined levels of deoxygenated hemoglobin as a surrogate measure of hematocrit. Additionally, an alert can be triggered when a change in Hb exceeds a corresponding threshold.

This summary is not intended to be a complete description of the invention. Other features, aspects, objects and advantages of the invention can be obtained from a review of the specification, the figures, and the claims.

BRIEF DESCRIPTION OF THE DRAWINGS

FIG. 1A is a top view of an optical sensor module (OSM), according to an embodiment of the present invention. FIG. 1B is a side view of the OSM shown in FIG. 1A. FIG. 1C is an exemplary variation of the OSM of FIGS. 1A and 1B.

DETAILED DESCRIPTION

Figure 2:
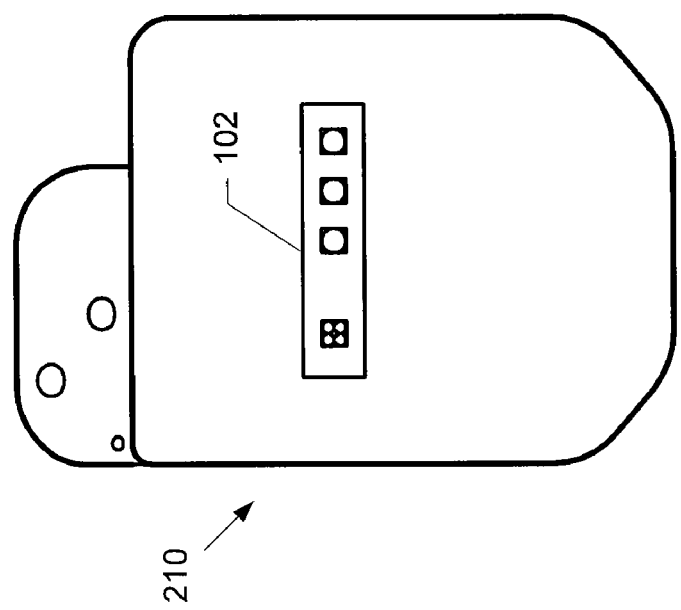
FIG. 2 illustrates how the OSM of FIGS. 1A and 1B can be attached to or incorporated into a housing of an implantable cardiac stimulation device.

The following description is of the best modes presently contemplated for practicing various embodiments of the present invention. This description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. Also, the left-most digit(s) of a reference number identifies the drawing in which the reference number first appears.

FIGS. 1A and 1B show an optical sensor module (OSM) 102, according to an embodiment of the present invention. The OSM 102 is shown as including four light sources 104a, 104b, 104c and 104d and three light detectors 114a, 114b and 114c. Depending on the specific implementation, the OSM 102 can include less or more light sources 104 and light detectors 114. It is even possible, though not preferably, that a single light detector 114 be used.

The light sources 104 are preferably light emitting diodes (LEDs), but can be other light sources such as, but not limited to, laser diodes and incandescent lamps. The light sources 104 and light detectors 114, are shown as being mounted to a substrate 110, and are enclosed in a hermetic, leak proof enclosure 112, consisting of a titanium housing with a light transparent quartz window, or encapsulated in a transparent slug (such as a clear epoxy resin). Where the light sources 104 are LEDs, there is preferably a collimator 106 that collimates the light of each LED. In accordance with a specific embodiment, the lights sources 104a, 104b, 104c and 104d generate light, respectively, of approximately 660 nm, 810 nm, 910 nm and 980 nm.

The configuration places the light sources that produce wavelengths having a greater absorption, assuming a high oxygen saturation ($S_{O2}$), closer to the light detector(s) 114. Additionally, the light sources 104a and 104b, which produce the 660 nm and 810 nm wavelengths used for calculating oxygen saturation, are preferably placed in a common y-axis relative to the light detector(s) 114. This configuration should provide for good accuracy, because is minimizes light intensity variations that may occur if light from the light sources 104a and 104b needed to travel different paths before reaching the detector(s) 114. For similar reasons, the light sources 104c and 104d, which produce the 910 nm and 980 nm wavelengths used for calculating hydration (as will be described below), are preferably also placed in a common y-axis relative to the light detector(s) 114. In other words, the configuration of FIGS. 1A and 1B are designed to minimize error due to different distances to the detectors. Nevertheless, alternative relative locations of the light sources 104 and light detector(s) are also within the scope of certain embodiments of the present invention. For example, a variation on the locations of the light sources 104a, 104b, 104c and 104d is shown in FIG. 1C.

FIG. 2 illustrates how the OSM 102 can be attached to a housing of an implantable cardiac stimulation device 210, which can be, e.g., a pacemaker and/or an implantable cardioverter-defibrillator (ICD). Exemplary details of how to attach a sensor module to an implantable cardiac stimulation device are described in U.S. patent application Ser. No. 10/913,942, entitled "Autonomous Sensor Modules for Patient Monitoring" (Turcott et al.), filed Aug. 4, 2004, which is incorporated herein by reference. It is also possible that the OSM 102 be integrally part of the implantable cardiac stimulation device 210. For example, the OSM can be located within the housing of an ICD (or pacemaker) that has a window through which light can be transmitted and detected. In a specific embodiment, the OSM 102 has a titanium frame with a light transparent quartz window that can be welded into a corresponding slot cut in the housing of the ICD. This will insure that the ICD enclosure with the welded OSM 102 will maintain an hermetic condition.

Figure 3:
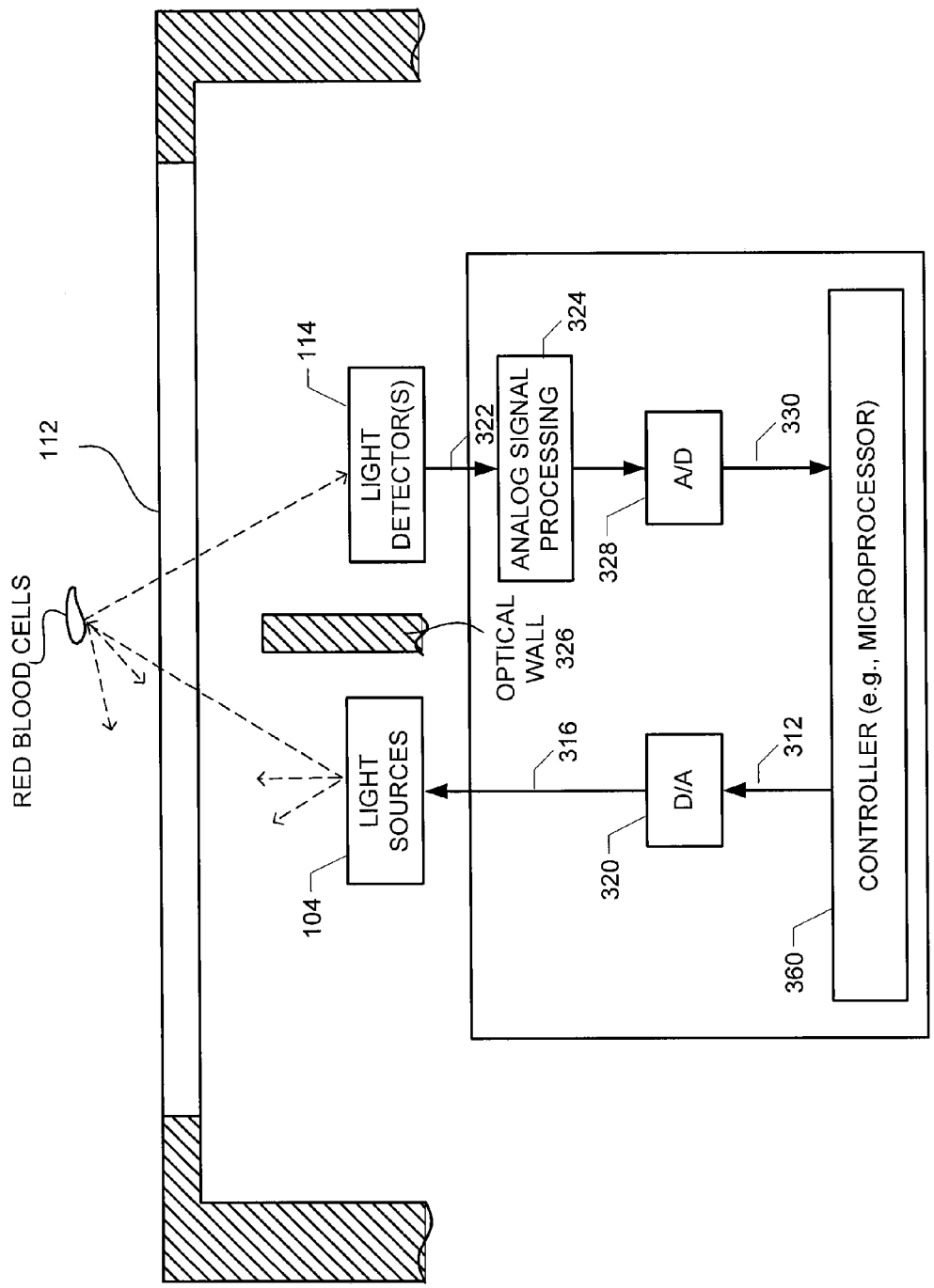
FIG. 3 is a high level block diagram that is useful for explaining the functioning of the OSM shown in FIGS. 1A and 1B.

FIG. 3 is a high level block diagram that is useful for explaining the functioning of the OSM 102 shown in FIGS. 1A and 1B. Referring to FIG. 3, each light source 104 transmits light having an intensity that is controlled by a corresponding drive signal 312/316. Such drive signal is controlled by a controller 360, which likely outputs a digital drive control signal 312 which is converted to an analog drive signal 316 by a digital-to-analog converter (D/A) 320. The controller 360 in this embodiment, and other embodiments, can be a microcontroller, a processor, a state machine, random logic, or the like.

In practice, the light sources 104a, 104b, 104c and 104d are serially energized, in a non-overlapping temporal relationship (i.e., in a time multiplexed manner). In the manner just described, the light of wavelengths of 660 nm, 810 nm, 910 nm and 980 nm are transmitted toward vascularized patient tissue that includes red blood cells.

When transmitted toward vascularized patient tissue, some of the light energy is scattered by blood. The different wavelengths are differently scattered, depending on the oxygen saturation, hemoglobin and/or hydration levels. After being scattered by blood, the interleaved light stream is received by the light detector(s) 114, which can produce a time multiplexed signal indicative of scattered light of the various wavelengths, or a separate signal for each of the wavelengths. An optional opaque optical wall 326 can be positioned between the light sources 104 and the light detector(s) 114, to reduce the chance that the light detector(s) 114 detect light directly from the light sources 104 (i.e., light that has not been scattered by blood).

At a high level, time multiplexing is used to produce a signal path for each of the different wavelengths of received light. Each signal path will typically include one or more filters (of analog signal processing block 324) and an A/D converter 328 to sample the received light signals. Using electronic circuitry, firmware and/or software, the received light signals can be analyzed so that oxygen saturation, hemoglobin concentration and hydration levels can be determined in accordance with embodiments of the present invention.

Also shown in FIG. 3 is the transparent material 112, which is shown as being a transparent window through which light of interest can exit and enter. Such a window can be made up of more than one distinct portion through which light of interest can exit and enter a housing. For example, light may exit a housing through a first portion of a window, while scattered light enters the housing through a second portion of the window, where the first and second portions of the window are not contiguous. In other words, the term window, as used herein, is intended to collectively encompass all portions of a housing through which light can enter and exit the housing, even if such portions are separated from one another (e.g., by opaque portions).

The light detector(s) 114 detect scattered light and produce a measurement signal 322 that is indicative of the intensity of the light detected by the light detector(s) 114. The measurement signal 322 is preferably filtered and amplified by the analog signal processing block 324 (e.g., which includes a filter and amplifier), and digitized by the analog-to-digital (A/D) converter 328, so that a digitized version 330 of the signal is provided to the controller 360. The portion of the measurement signal 322 corresponding to light of each wavelength can be filtered (e.g., band pass filtered) in more than one manner, so as to separate out different components of the measurement signal. This allows measures of both venous oxygen saturation ($S_{vO2}$) and arterial oxygen saturation ($S_{aO2}$) to be obtained, if desired, as described in more detail below.

There can be a separate D/A converter 320, receiving a separate drive signal 312, for each light source. Alternatively, the controller 360 can output a time multiplexed drive signal 312 that is provided to a single D/A converter 320, and a demultiplexer can be provided at the output of the D/A converter 320. Such a demultiplexer will provide the analog version of the drive signal to the appropriate light source 104. Similarly, outputs of the light detector(s) 114 are provided to an analog signal processing block 324, the output of which is provided to an A/D converter 328.

Figure 4:
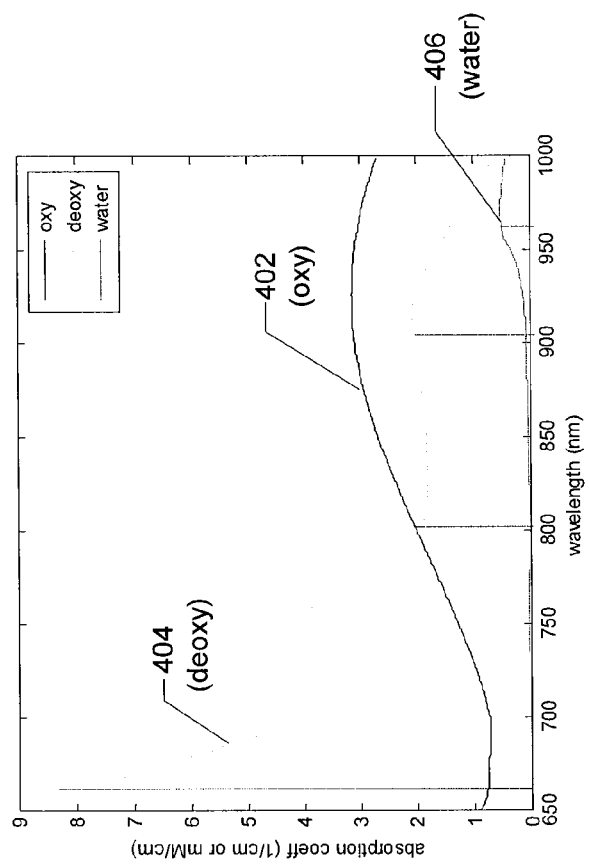
FIG. 4 is a graph of chromophore's spectrums for oxygenated hemoglobin, deoxygenated hemoglobin and water.

FIG. 4 is a graph of chromophore's spectrums for oxygenated hemoglobin (HbO, as referred to as "oxy"), deoxygenated hemoglobin (Hb, also referred to as "deoxy") and water. More specifically, FIG. 4 includes three curves indicative of absorption coefficients of oxygenated hemoglobin, deoxygenated hemoglobin and water at different wavelengths. Curve 402 illustrates the absorption spectra for oxygenated hemoglobin; curve 404 illustrates the absorption spectra for deoxygenated hemoglobin; and curve 406 illustrates the absorption spectra for water.

As can be appreciated from FIG. 4, for the 660 nm light generated by the light source 104a, deoxygenate hemoglobin is the primary absorber. The 810 nm light generated by the light source 104b, is the isobestic wavelength. For the 910 nm light generated by the light source 104c, oxygenated hemoglobin is the primary absorber. For the 960 nm light generated by the light source 104d, water is the primary absorber.

Figure 5:
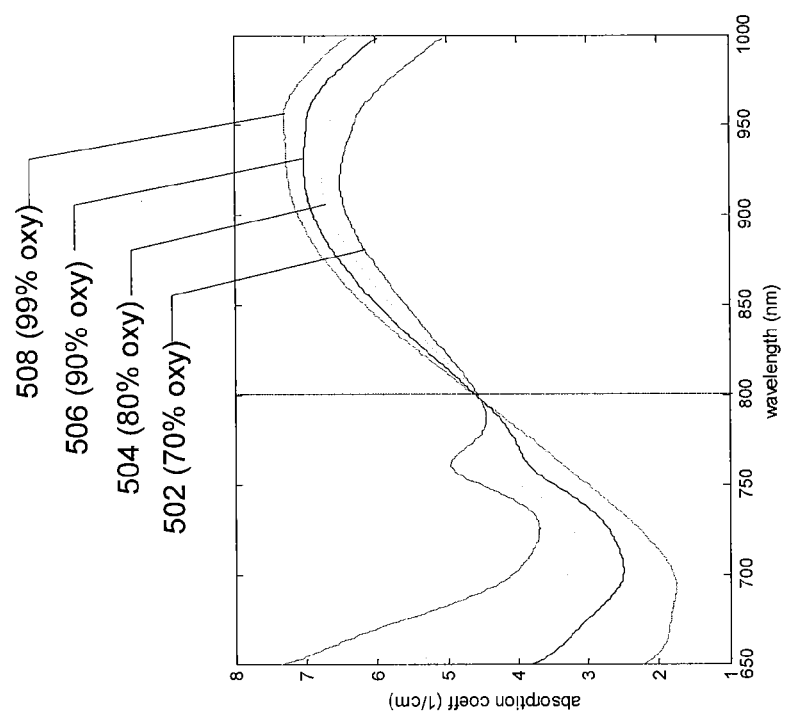
FIG. 5 is a graph of an example blood spectrum with varying oxygen saturation values, assuming a homogenous mixture of each chromophore.

Using the data of FIG. 4, and assuming a homogenous mixture of each chromophore, an example blood spectrum with varying oxygen saturation values is shown in FIG. 5. Curve 502 illustrates the absorption spectra for 70% oxygenated hemoglobin; curve 504 illustrates the absorption spectra for 80% oxygenated hemoglobin; curve 506 illustrates the absorption spectra for 90% oxygenated hemoglobin; and curve 508 illustrates the absorption spectra for 99% oxygenated hemoglobin. As can be appreciated from FIG. 5, the absorption value at the isobestic wavelength (about 810 nm) does not change for different oxygen saturation values. Thus, the isobestic wavelength does not provide useful information for oxygenation levels. However, the isobestic wavelength is useful for measuring hemoglobin concentration levels, as will be described below.

A benefit of using the four wavelength OSM 102 is that pulsatile oxygen saturation, tissue oxygen saturation, hemoglobin concentration, and changes in hydration can all be monitored using common types of detectors 114 (i.e., Silicon photo detectors), as will be described in more detail below.

Discussed below are algorithms that are used to calibrate the OSM 102 and to determine pulsatile oxygen saturation, tissue oxygen saturation, hemoglobin concentration, and hydration levels.

Pulsatile Oxygen Saturation

Pulsatile oxygen saturation refers to the oxygen saturation in both the arteries and veins, and thus may also be referred to as blood vessel oxygen saturation. To determine pulsatile saturation, a diffusion algorithm is utilized to find the absorption coefficient of tissue. However due to the constraints imposed by the OSM 102 and resulting calibrations using a tissue phantom, these values cannot be directly used to find absolute oxygen saturation. However, these values are sufficient for calibration purposes, as well as for detecting relative changes in oxygen saturation. Using the calculated absorption and approximated reduced scattering coefficients eliminate the need for calibration. Such a diffusion algorithm is shown below in Equation 1 (Eq 0.1)

$$\beta(\lambda) = \frac{1}{2}\sqrt{\left(\frac{3\mu_s'^p(\lambda)}{\mu_a^v(\lambda)}\right)}\left(1 - \frac{1}{1 + \rho\sqrt{3\mu_s'^v(\lambda)\mu_a^v(\lambda)}}\right) \qquad (Eq.\ 1)$$

where $\beta(\lambda)$ is the calibration coefficient for a given wavelength $\lambda$, and $\mu_s'$ and $\mu_a$ are the reduced scattering and absorption coefficients at a given wavelength ($\lambda$). The superscripts p and v refer to, respectively, the peak and valley of the pulsatile signal, and $\rho$ is the source-detector distance.

Using this optical property-based calibration coefficient, the pulsatile oxygen saturation ($S_{O2}$) is found by Equation 2 (Eq. 2) below $$S_{O2} = \frac{k_{Hb}^{910} R\left(\frac{\beta^{910}}{\beta^{660}}\right) - k_{Hb}^{660}}{k_{HbO}^{660} - k_{Hb}^{660} - R\left(\frac{\beta^{910}}{\beta^{660}}\right)(k_{HbO}^{910} - k_{Hb}^{910})} \qquad (Eq.\ 2)$$

where k is the known molar absorption coefficient of oxygenated hemoglobin (HbO) and deoxygenated hemoglobin (Hb) at a given wavelength, and R is a ratio defined by Equation 3 (Eq. 3) below $$R = \frac{\ln\left(\frac{I^v(660)}{I^p(660)}\right)}{\ln\left(\frac{I^v(910)}{I^p(910)}\right)} \quad \text{(Eq. 3)}$$

where $I^v(\lambda)$ is the minimum measured light intensity of wavelength $\lambda$ within one cardiac or respiratory cycle, and $I^p(\lambda)$ is the maximum measured light intensity of wavelength $\lambda$ within one cardiac or respiratory cycle. Variations in light intensity within a cardiac cycle are relevant to arterial oxygen saturation ($S_{aO2}$), and variations in light intensity within a respiratory cycle are relevant to venous oxygen saturation ($S_{vO2}$), as explained in more detail below. Since the ratio of the calibration coefficients is being used, errors due to the geometry of the OSM 102 are reduced, or even cancelled out. Additionally, since k and β are known for the various wavelengths, a determination of $S_{O2}$ using the Equations above can be implementing using a look-up table, or the like, if desired.

Equation 2 above can be used to determine both arterial oxygen saturation ($S_{aO2}$) and venous oxygen saturation ($S_{vO2}$). In other words, the $S_{O2}$ in Equation 2 can be $S_{aO2}$ or $S_{vO2}$. Arteries have a time-varying component that corresponds to the heart rate. In other words, every time the heart beats, new oxygenated blood is forced through the arteries, which causes the measured optical signal to drop. Veins have a similar time-varying component that corresponds to the respiratory rate of the subject (rather than to heart rate). Since patient's typically breathe much slower than their heart beats, filters can be used to separate the variations in the optical signal due to cardiac and respiratory pulsations, thereby enabling separate determinations of $S_{vO2}$ and $S_{aO2}$. For example, band pass filters can be used to filter the optical signal at each wavelength, to separate out these time-varying components. The unchanging portion of the signal is assumed to be primarily due to the hemoglobin within the tissue.

Tissue Oxygen Saturation

In accordance with specific embodiments of the present invention, oxygenated hemoglobin (HbO) concentration levels and deoxygenated hemoglobin (Hb) concentration levels can be determined using Equation 4 (Eq. 4) below.

$$\begin{vmatrix} [HbO] \\ [Hb] \end{vmatrix} P.L. = \begin{vmatrix} k_{HbO}^{660} & k_{Hb}^{660} \\ k_{HbO}^{910} & k_{Hb}^{910} \end{vmatrix}^{-1} \begin{vmatrix} \ln\left(\frac{I(660)}{I_0(660)}\right) \\ \ln\left(\frac{I(910)}{I_0(910)}\right) \end{vmatrix} \quad \text{(Eq. 4)}$$

where k is the known molar absorption coefficient of oxygenated hemoglobin (HbO) and deoxygenated hemoglobin (Hb) at a given wavelength, [HbO] and [Hb] are the concentrations of oxygenated and deoxygenated hemoglobin, P.L. is effective path length for photons traveling through the tissue, $I(\lambda)$ is the initial intensity of light of wavelength $\lambda$ (i.e., before scattering) and $I_0(\lambda)$ is the measured intensity of light of wavelength $\lambda$ (i.e., after scattering).

After using Equation 4 to solve for [HbO] and [Hb], tissue oxygen saturation ($S_{tO2}$) can be found by Equation 5 (Eq. 5) below, assuming the path length is about the same for each wavelength. Such an assumption is valid when using the OSM 102 of the present invention.

$$S_{tO2} = \frac{[HbO]}{[HbO] + [Hb]}. \quad \text{(Eq. 5)}$$

It noted that this algorithm does not take into account changes in scattering due, e.g., due to tissue growth over the OSM 102. Because of this the tissue saturation should be calibrated for. This can be accomplished by assuming tissue saturation should be 80%. Other techniques for calibrating optical sensors are described, e.g., in U.S. patent application Ser. No. 11/282,198, entitled "Implantable Self-Calibrating Optical Sensors", filed Nov. 17, 2005 (Poore), which is incorporated herein by reference.

Hemoglobin Concentration

In accordance with specific embodiments of the present invention, the hemoglobin concentration for tissue can be determined using the 810 nm light source (104*b* in FIGS. 1A and 1B) and Equation 6 (Eq. 6) below.

$$[H] = \frac{\ln\left(\frac{I(810)}{I_0(810)}\right)}{k_{HbO}^{810} S_{tO2} + k_{Hb}^{810}(1 - S_{tO2})} \quad \text{(Eq. 6)}$$

where [H] is the hemoglobin concentration for tissue, k is the known molar absorption coefficient of oxygenated hemoglobin (HbO) and deoxygenated hemoglobin (Hb) at a given wavelength, $I_0(810)$ is the initial intensity of light of wavelength 810 nm (i.e., before scattering) and $I(810)$ is the measured intensity of light of wavelength 810 nm (i.e., after scattering). The initial intensity of light, $I_o$, can be found, e.g., by measuring the optical power output of a light source in an integrating sphere for a given input electrical power. This is done to establish a relationship between a light source's output intensity and various electrical input powers. Other techniques for measuring initial intensities of light are also possible, and within the scope of the present invention.

These values are calculated at 810 nm (the isobestic wavelength) to minimize the affects of oxygen saturation on the calculated concentration of hemoglobin. This can be appreciated from the above discussions of FIGS. 4 and 5.

Hydration

Specific embodiments of the present also provide for the monitoring of tissue hydration (% w). The derivation below explains how specific methods of the present invention were derived.

It is known from Beer's law or the diffusion equation that changes in tissue optical properties will affect the measured intensity by the OSM detector(s) exponentially. If it is assumed that intensity counts produced by the OSM are linearly related to the power incident on the detector(s), this relationship can be written as shown in Equation 7a (Eq. 7a) below.

$$f(\ln(I)) = \mu_{a\_w}(\%w) + \left(k_{HbO}\left(\frac{S_{tO2}}{100}\right) + k_{Hb}\left(1 - \frac{S_{tO2}}{100}\right)\right)[H] \quad \text{(Eq. 7a)}$$

where f is some unknown function, $\mu_{a\_w}$ is the known absorption coefficient of water, and $k_{Hbo}$ and $k_{Hb}$ are known molar absorption coefficients of oxygenated hemoglobin and deoxygenated hemoglobin respectively. [H] is the hemoglobin concentration, e.g., as determined using Eq. 6 above. The variable can be assumed to be I, which is the normalized intensity at the detector, where $$I = \frac{I(980)}{I_0(980)}$$

for 980 nm light. Thus, Equation 7a can be rewritten as Equation 7b shown below.

$$f\left(\ln\left(\frac{I(980)}{I_0(980)}\right)\right) = \mu_{a\_w}^{980}(\%\ w) + \left(k_{Hbo}^{980}\left(\frac{S_{tO2}}{100}\right) + k_{hb}^{980}\left(1 - \frac{S_{tO2}}{100}\right)\right)[H] \quad \text{(Eq. 7b)}$$

Before continuing, Equation 8a (Eq. 8a) below should be understood.

$$-\ln\left(\frac{I}{I_0}\right) = \ln(I_0) - \ln(I) = \quad \text{(Eq. 8a)}$$
$$\ln(I_0) - \ln(counts \cdot conver) = \ln(I_0) - \ln(counts) - \ln(conver)$$

where conver is the linear conversion factor used to find the intensity of light from the OSM counts. Using this, Beer's law can be written as Equation 9 (Eq. 9) below $$-\ln\left(\frac{I}{I_0}\right) = \ln(I_0) - \ln(counts) - \ln(conver) = \quad \text{(Eq. 9)}$$
$$\mu_{a\_w}(\%\ w) + \left(k_{Hbo}\left(\frac{S_{tO2}}{100}\right) + k_{Hb}\left(1 - \frac{S_{tO2}}{100}\right)\right)[H].$$

When using light having a 980 nm wavelength, as is done in accordance with specific embodiments of the present invention, Equation 8a can be rewritten as Equation 8b shown below.

$$-\ln\left(\frac{I(980)}{I_0(980)}\right) = \ln(I_0(980)) - \ln(I) = \quad \text{(Eq. 8b)}$$
$$\ln(I_0(980)) - \ln(counts(980) \cdot conver(980)) =$$
$$\ln(I_0(980)) - \ln(counts(980)) - \ln(conver(980))$$

Based on the Equation 9 above, specific embodiments of the present invention use the following algorithm for monitoring changes in hydration (also referred to as tracking hydration changes). First, an initial value for the hydration is calculated in accordance with Equation 10 (Eq. 10) below.

$$W_0 = \frac{\ln(counts(980)) - \left(k_{HbO}\left(\frac{S_{tO2}}{100}\right) + k_{hb}\left(1 - \frac{S_{tO2}}{100}\right)\right)[H]}{\mu_{a\_w}^{980}} \quad \text{(Eq. 10)}$$

where counts are the measured A/D values returned by the OSM 102 with the dark current subtracted out. For example, referring back to FIG. 3, the counts can be determined using the A/D 328.

After this value is calculated, all other subsequent 980 nm wavelength intensity measurements can be utilized to find changes in the hydration levels, in accordance with Equation 11 (Eq. 11) below.

$$\Delta W = W_0 - \frac{\ln(counts(980)) + \left(k_{Hbo}\left(\frac{S_{tO2}}{100}\right) + k_{Hb}\left(1 - \frac{S_{tO2}}{100}\right)\right)[H]}{\mu_{a\_w}^{980}}. \quad \text{(Eq. 11)}$$

It is noted that the values will be unitless, and that calculations are not absolute, but rather are relative.

While water actually has its peak absorption at about 1450 nm, water also has a substantial absorption peak at about 980 nm, as was explained with reference to FIG. 4. Thus, while it may be optimal to use a 1450 nm light source to monitor hydration, use of a 1450 nm light source would not enable a goal of certain embodiments of the present invention, which is to use a single type of light detector 114 to detect light of all the wavelengths being transmitted (which also includes light of approximately 660 nm, 810 nm, 910 nm, as explained above). If 1450 nm light were used to detect changes in hydration, then a Gallium Arsenide photodetector would be required to detect light of such a high wavelength, because a Silicon photodetector can not detect light of 1450 nm very well. However, a Gallium Arsenide photodetector is not good at detecting light of 660 nm, 810 nm and 910 nm, which wavelengths are used to monitoring oxygen saturation and hemoglobin concentration levels. A benefit of using a 980 nm light source (as opposed to a 1450 nm light source) to monitor hydration is that Silicon photodetectors can be used detect light of 660 nm, 810 nm, 910 nm and 980 nm, thereby allowing a single type of photodetector to be used for monitoring oxygen saturation and hemoglobin concentration, as well as hydration. In other words, using scattering of 980 nm light to detect hydration, enables a single type of light detector 114 to be used.

Pulmonary Edema Detection

In accordance with specific embodiments of the present invention, changes in hydration are monitored for the purpose of detecting pulmonary edema, which is caused by fluid accumulation in the lungs. As fluid increases in the lungs, it is believed that fluid will also increase in the chest cavity where the OSM 102 is implanted. Thus, increases in hydration, as detected by the OSM 102, can be interpreted as being indicative of pulmonary edema. In this manner, the OSM 102 can track worsening (as well as improving) pulmonary edema. This will enable a caregiver to prescribe medications to treat the pulmonary edema, and to monitor the efficacy of such treatments.

More specifically, one or more response can be triggered in response to an increase or percentage change in hydration beyond a corresponding threshold, which is inductive of pulmonary edema. In accordance with an embodiment of the present invention, information related to hydration can be stored. Such information can be continually, or from time to time, automatically uploaded to an external device. Such an external device can be located, e.g., in the patients' home, and the information can be transmitted (e.g., through telephone lines or the Internet) to a medical facility where a physician can analyze the information. Alternatively, the external device can be located at a medical facility, and the information can be uploaded when the patient visits the facility.

In some embodiments, a patient is alerted (e.g., using an alert 608 in FIG. 6B) when an increase or percentage change in hydration beyond a corresponding threshold occurs, which is inductive of pulmonary edema. Such an alert could be a vibratory or auditory alert that originates from within an implantable device (e.g., 210). Alternatively, the implantable device may wirelessly transmit an alert to an external device that produces a visual or auditory alert that a patient can see or hear. The alert may inform the patient to take medication or contact a caregiver (e.g., physician). In still another embodiment, a caregiver (e.g., physician, clinician) is alerted whenever the presence of pulmonary edema is detected.

In further embodiments, therapy can be triggered in response to detecting an increase or percentage change in hydration beyond a corresponding threshold. For example, if the implanted device is appropriately equipped, it can titrate appropriate drug therapy. These are just a few examples of the types of responses that can be performed upon detecting a surrogate of pulmonary edema. One of ordinary skill in the art would understand from the above description that other response are also possible, while still being within the spirit and scope of the present invention.

Anemia Detection

In accordance with specific embodiments of the present invention, changes in hematocrit are monitored for the purpose of detecting anemia, which is a deficiency of red blood cells (RBCs). Anemia is a common blood disorder where there is a lower than normal number of red blood cells in the blood, usually measured by a decrease in the amount of hemoglobin. Hemoglobin is the oxygen-carrying part of red blood cells, which gives these blood cells their red color.

Patients with Heart Failure (HF) may have an associated problem of anemia. A low hematocrit level (RBC %) limits the amount of oxygen being carried to the body, which makes the heart work harder. As the severity of HF progresses, the findings of anemia increase, and severe anemia due to any cause can worsen HF. Typically, there is a higher rate of mortality in HF patients that have hematocrit levels in the 20-30% range, than those in the 40-50% range.

The most common in vitro measurement of anemia is to take a blood sample of known volume and measure the percent of red blood cells in the volume, known as the hematocrit measurement. In accordance with embodiments of the present invention, in vivo measurements of anemia can be taken, as will be described below.

As described above, e.g., in the discussion of Equation 4, the OSM 102 can produce in vivo measurements of oxygenated hemoglobin (HbO) and deoxygenated hemoglobin (Hb). In accordance with specific embodiments of the present invention, such OSM measurements of Hb can be used as a surrogate measure of changes in hematocrit, since changes in Hb are believed to be proportional to changes in hematocrit. Thus, reductions in detected levels of Hb can be interpreted as reductions in hematocrit, and vice versa. In this manner, the OSM 102 can track worsening (as well as improving) anemia in a patient (e.g., an HF patient). This will enable a care giver to prescribe medications to treat the anemia, and to monitor the efficacy of such treatments.

More specifically, one or more response can be triggered in response to a reduction or percentage change in Hb concentration beyond a corresponding threshold, which is inductive of anemia. In accordance with an embodiment of the present invention, information related to the Hb concentration can be stored. Such information can be continually, or from time to time, automatically uploaded to an external device. Such an external device can be located, e.g., in the patients' home, and the information can be transmitted (e.g., through telephone lines or the Internet) to a medical facility where a physician can analyze the information. Alternatively, the external device can be located at a medical facility, and the information can be uploaded when the patient visits the facility.

In some embodiments, a patient is alerted (e.g., using an alert 608 in FIG. 6B) when a reduction or percentage change in Hb concentration beyond a corresponding threshold occurs, which is inductive of anemia. Such an alert could be a vibratory or auditory alert that originates from within an implantable device (e.g., 210). Alternatively, the implantable device may wirelessly transmit an alert to an external device that produces a visual or auditory alert that a patient can see or hear. The alert may inform the patient to take medication or contact a caregiver (e.g., physician). In still another embodiment, a caregiver (e.g., physician, clinician) is alerted whenever the presence of anemia is detected.

In further embodiments, therapy can be triggered in response to detecting a reduction or percentage change in Hb concentration beyond a corresponding threshold. For example, if the implanted device is appropriately equipped, it can titrate appropriate drug therapy. These are just a few examples of the types of responses that can be performed upon detection of a surrogate of anemia. One of ordinary skill in the art would understand from the above description that other response are also possible, while still being within the spirit and scope of the present invention.

Exemplary Stimulation Device

The OSM 102 can be implanted in a patient by itself, or, as mentioned above in the discussion of FIG. 2, the OSM 102 can be can be attached to a housing of an implantable cardiac stimulation device (e.g. 210). Such an implantable cardiac stimulation device can be, e.g., a pacemaker and/or an implantable cardioverter-defibrillator (ICD). An example of such a stimulation device will now be described with reference to FIGS. 6A and 6B.

Figure 6A:
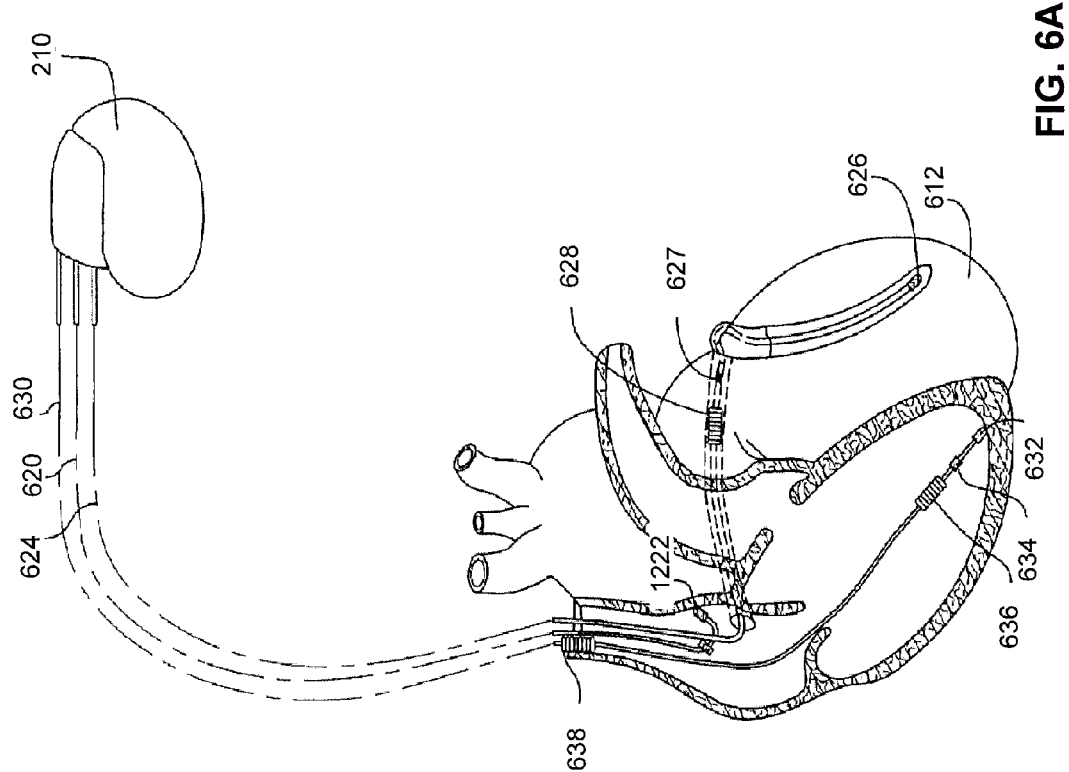
FIG. 6A illustrates an exemplary implantable cardiac stimulation device in electrical communication with a patient's heart by way of three leads, which are suitable for delivering multi-chamber stimulation and shock therapy.

Referring to FIG. 6A, the exemplary implantable stimulation device 210 is shown as being in electrical communication with a patient's heart 612 by way of three leads, 620, 624 and 630, suitable for delivering multi-chamber stimulation and shock therapy. The sensor module 802 of the present invention can be placed within any of these leads, as was described above. Alternatively, a further dedicated lead or catheter can be provided for the purpose of containing the sensor 802 and placing the sensor 802 at a desired measurement site.

To sense atrial cardiac signals and to provide right atrial chamber stimulation therapy, the stimulation device 210 is coupled to an implantable right atrial lead 620 having at least an atrial tip electrode 622, which typically is implanted in the patient's right atrial appendage.

To sense left atrial and ventricular cardiac signals and to provide left-chamber pacing therapy, the stimulation device 210 is coupled to a "coronary sinus" lead 624 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

The exemplary coronary sinus lead 624 is designed to receive atrial and ventricular cardiac signals and to deliver left ventricular pacing therapy using at least a left ventricular tip electrode 626, left atrial pacing therapy using at least a left atrial ring electrode 627, and shocking therapy using at least a left atrial coil electrode 628.

The stimulation device 210 is also shown in electrical communication with the patient's heart 612 by way of an implantable right ventricular lead 630 having, in this embodiment, a right ventricular tip electrode 632, a right ventricular ring electrode 634, a right ventricular (RV) coil electrode 636, and an SVC coil electrode 638. Typically, the right ventricular lead 630 is transvenously inserted into the heart 612 so as to place the right ventricular tip electrode 632 in the right ventricular apex so that the RV coil electrode 636 will be positioned in the right ventricle and the SVC coil electrode 638 will be positioned in the superior vena cava. Accordingly, the right ventricular lead 630 is capable of receiving cardiac signals and delivering stimulation in the form of pacing and shock therapy to the right ventricle.

Figure 6B:
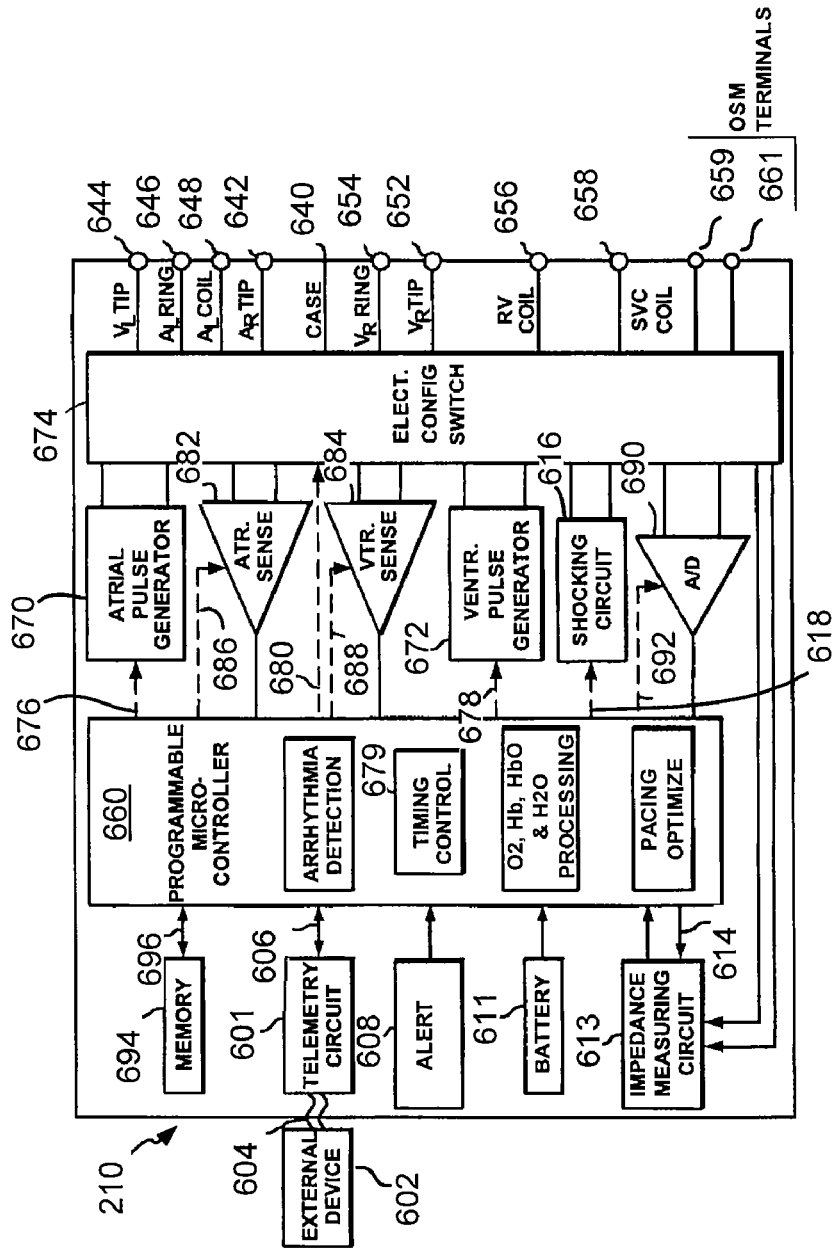
FIG. 6B is a simplified block diagram of the multi-chamber implantable stimulation device of FIG. 6A.

As illustrated in FIG. 6B, a simplified block diagram is shown of the multi-chamber implantable stimulation device 210, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 640 for the stimulation device 210, shown schematically in FIG. 6B, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 644, 646, 648, 652, 654, 656, and 658 (shown schematically and, for convenience, the names of the electrodes to which they are connected are shown next to the terminals).

As such, to achieve right atrial sensing and pacing, the connector includes at least a right atrial tip terminal (AR TIP) 642 adapted for connection to the atrial tip electrode 622.

To achieve left chamber sensing, pacing and shocking, the connector includes at least a left ventricular tip terminal (VL TIP) 644, a left atrial ring terminal (AL RING) 646, and a left atrial shocking terminal (AL COIL) 648, which are adapted for connection to the left ventricular tip electrode 626, the left atrial ring electrode 627, and the left atrial coil electrode 628, respectively.

To support right chamber sensing, pacing and shocking, the connector further includes a right ventricular tip terminal (VR TIP) 652, a right ventricular ring terminal (VR RING) 654, a right ventricular shocking terminal (RV COIL) 656, and an SVC shocking terminal (SVC COIL) 658, which are adapted for connection to the right ventricular tip electrode 632, right ventricular ring electrode 634, the RV coil electrode 636, and the SVC coil electrode 638, respectively.

The connector is also shown as including terminals 659 and 661 (OSM TERMINALS), which can be used to connect to an optical sensor module 102 of embodiments of the present invention. More or less than two terminals can be included, depending upon how the OSM 102 is designed. Such terminals may be used where the OSM 102 is attached to the housing If the OSM 102 is incorporated into the device 210, there may be no need for such OSM terminals.

At the core of the stimulation device 210 is a programmable microcontroller 660 which controls the various modes of stimulation therapy, including pacing optimization and anti-arrhythmia therapy. Such a microcontroller 660 can include, e.g., one or more processor. The microcontroller 660 can also be used to measure levels of blood oxygen saturation, tissue oxygen saturation, hemoglobin concentration, tissue hydration based on the detected scattered light, based on scattered light detected by the OSM 102. Such measures can be used, e.g., for pacing optimization, disease monitoring, and the like. Additionally or alternatively, the measures can be stored in memory 694 for later transmission to an external device 602 using the telemetry circuit 601.

If the OSM 102 provides analog signals to the implantable device, then the terminals 659 and 661, through switch 674, can provide such signals to an analog-to-digital (A/D) converter 690 that converts the signals to a digital format understood by the microcontroller 660. It is also possible that a dedicated A/D converter (e.g., 318) be provided within the implantable stimulation device 210 for the purpose of digitizing signals received from the OSM 102. If the OSM 102 provides digital signals to the implantable device 210, then such signals may be provided directly to the microcontroller 660, assuming it is the microcontroller 660 that performs the processing that determines measures of blood oxygen saturation, tissue oxygen saturation, hemoglobin concentration and/or tissue hydration based on the signals. It is also possible that the implantable device 210 include circuitry, external to the microcontroller 660, which is dedicated to determining measures of blood oxygen saturation, tissue oxygen saturation, hemoglobin concentration and/or tissue hydration.

As is well known in the art, the microcontroller 660 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 660 includes the ability to analyze signals (data) as controlled by a program code stored in a designated block of memory. The details of the design of the microcontroller 660 are not critical to the present invention. Rather, any suitable microcontroller 660 can be used to carry out the functions described herein. The use of microprocessor-based control circuits for performing timing, control and data analysis functions are well known in the art.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the stimulation device and their inter-relationship, see U.S. Pat. No. 4,788, 980 (Mann et. al.). The '052, '555, '298 and '980 patents are incorporated herein by reference.

As shown in FIG. 6B, an atrial pulse generator 670 and a ventricular pulse generator 672 generate pacing stimulation pulses for delivery by the right atrial lead 620, the right ventricular lead 630, and/or the coronary sinus lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators, or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry 679 which is used to control pacing parameters (e.g., the timing of stimulation pulses) as well as to keep track of the timing of refractory periods, PVARP intervals, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 674 includes a plurality of switches for connecting the desired electrodes to the appropriate I/O circuits, thereby providing complete electrode programmability.

Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art. The switch 674 can also be used to connect wires from an oximetry sensor 802 to appropriate I/O circuits.

Atrial sensing circuits 682 and ventricular sensing circuits 684 may also be selectively coupled to the right atrial lead 620, coronary sinus lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers, or shared amplifiers. The switch 674 determines the "sensing polarity" of the cardiac signal by selectively closing the appropriate switches, as is also known in the art. In this way, the clinician may program the sensing polarity independent of the stimulation polarity.

Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables the device 210 to deal effectively with the difficult problem of sensing the low amplitude signal characteristics of atrial or ventricular signals.

The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity, in the appropriate chambers of the heart. The sensing circuits, 682 and 684, in turn, receive control signals over signal lines, 686 and 688, from the microcontroller 660 for purposes of measuring cardiac performance at appropriate times, and for controlling the gain, threshold, polarization charge removal circuitry (not shown), and timing of any blocking circuitry (not shown) coupled to the inputs of the sensing circuits, 682 and 686.

For arrhythmia detection, the device 210 utilizes the atrial and ventricular sensing circuits, 682 and 684, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the microcontroller 660 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 210. The data acquisition system 690 is coupled to the right atrial lead 620, the coronary sinus lead 624, and the right ventricular lead 630 through the switch 674 to sample cardiac signals across any pair of desired electrodes.

Advantageously, the data acquisition system 690 can be coupled to the microcontroller 660, or other detection circuitry, for detecting an evoked response from the heart 612 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 660 detects a depolarization signal during a window following a stimulation pulse, the presence of which indicates that capture has occurred. The microcontroller 660 enables capture detection by triggering the ventricular pulse generator 672 to generate a stimulation pulse, starting a capture detection window using the timing control circuitry 679 within the microcontroller 660, and enabling the data acquisition system 690 via control signal 692 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 660 is further coupled to a memory 694 by a suitable data/address bus 696, wherein the programmable operating parameters used by the microcontroller 660 are stored and modified, as required, in order to customize the operation of the stimulation device 210 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 612 within each respective tier of therapy.

Data acquired by the data acquisition system 690 (and optionally stored) can be used for subsequent analysis to guide the programming of the device and/or to monitor oxygen saturation and/or hematocrit, appropriately adjust pacing interval parameters, select optimum pacing intervals, and/or select appropriate anti-arrhythmia therapy.

Advantageously, the operating parameters of the implantable device 210 may be non-invasively programmed into the memory 694 through a telemetry circuit 601 in telemetric communication with the external device 210, such as a programmer, transtelephonic transceiver, or a diagnostic system analyzer. The telemetry circuit 601 is activated by the microcontroller by a control signal 606. The telemetry circuit 601 advantageously allows intracardiac electrograms, oxygen saturation information, hematocrit information and status information relating to the operation of the device 210 (as contained in the microcontroller 660 or memory 694) to be sent to an external device 210 through an established communication link 604.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (note: this relates to transfer of EGM data) (McClure et al.), which patents are hereby incorporated herein by reference.

The stimulation device 210 can further include one or more physiologic sensors, which can be located within the stimulation device housing 640 as shown, or can be located external to the housing.

Additionally, the device 210 can include one or more alerts 608, which can be triggered, e.g., to inform that patient of a sudden decrease in the blood oxygen saturation level, a gradual decrease in the hemoglobin (hematocrit) concentration that would indicate a worsening of the patient's anemic condition, or a gradual increase in the pectoral tissue hydration in close proximity to the OSM 102 that would indicate the onset of pulmonary edema.

The stimulation device 210 additionally includes a battery 612 which provides operating power to all of the circuits shown in FIG. 6B. For the stimulation device 210, which employs shocking therapy, the battery 612 must be capable of operating at low current drains for long periods of time, and then be capable of providing high-current pulses (for capacitor charging) when the patient requires a shock pulse. The battery 612 should also have a predictable discharge characteristic so that elective replacement time can be detected. Accordingly, the device 210 preferably employs lithium/silver vanadium oxide batteries, but is not limited thereto.

The stimulation device 210 can further include a magnet detection circuitry (not shown), coupled to the microcontroller 660. It is the purpose of the magnet detection circuitry to detect when a magnet is placed over the stimulation device 210, which magnet may be used by a clinician to perform various test functions of the stimulation device 210 and/or to signal the microcontroller 660 that the external programmer 210 is in place to receive or transmit data to the microcontroller 660 through the telemetry circuits 601.

As further shown in FIG. 6B, the device 210 is shown as having an impedance measuring circuit 613 which is enabled by the microcontroller 660 via a control signal 614. The known uses for an impedance measuring circuit 613 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; measuring thoracic impedance for detecting and assessing the severity of pulmonary edema; detecting when the device has been implanted; measuring stroke volume; and detecting the opening of heart valves, etc. The impedance measuring circuit 613 is advantageously coupled to the switch 674 so that any desired electrode may be used. In addition, to facilitate the measurement of peripheral tissue edema, extra electrodes can be added to the device housing, thereby limiting the test electric field to the peripheral tissue.

In the case where the stimulation device 210 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 660 further controls a shocking circuit 616 by way of a control signal 618. The shocking circuit 616 generates shocking pulses of low (up to 0.5 Joules), moderate (0.5-10 Joules), or high energy (6 to 40 Joules), as controlled by the microcontroller 660. Such shocking pulses are applied to the patient's heart 612 through at least two shocking electrodes, and as shown in this embodiment, selected from the left atrial coil electrode 628, the RV coil electrode 636, and/or the SVC coil electrode 638. As noted above, the housing 640 may act as an active electrode in combination with the RV electrode 636, or as part of a split electrical vector using the SVC coil electrode 638 or the left atrial coil electrode 628 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized to be recognize), and pertaining exclusively to the treatment of ventricular fibrillation. Accordingly, the microcontroller 660 is capable of controlling the synchronous or asynchronous delivery of the shocking pulses. Another approach to electrical anti-arrhythmia therapy is anti-tachycardia pacing, in which low-voltage pacing pulses are applied to pace-terminate the arrhythmia. This approach is particularly effective in low rate ventricular tachycardias.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. An implantable system, comprising:
a plurality of light sources to transmit toward vascularized tissue, in a time multiplexed manner, light having a first wavelength of approximately 660 nm, light having a second wavelength of approximately 810 nm, light having a third wavelength of approximately 910 nm, and light having a fourth wavelength of approximately 980 nm;
one or more silicon light detector to detect light of the first, second, third and fourth wavelengths scattered by the vascularized tissue; and
one or more processor configured to
determine levels of blood oxygen saturation based on the detected scattered light of the first and third wavelengths;
determine levels of tissue oxygen saturation based on the detected scattered light of the first and third wavelengths;
determine levels of hemoglobin concentration for tissue based on the detected scattered light of the second wavelength; and
determine levels of tissue hydration based on the detected scattered light of the fourth wavelength.

2. The implantable system of claim 1, wherein the plurality of light sources include:
a first light source configured to transmit light having the first wavelength of approximately 660 nm;
a second light source configured to transmit light having the second wavelength of approximately 810 nm;
a third light source configured to transmit light having the third wavelength of approximately 910 nm; and
a fourth light source configured to transmit light having the fourth wavelength of approximately 980 nm;
wherein the first and third light sources are located relative to one another and relative to the one or more silicon light detector so that path lengths from the first light source to the one or more silicon light detector, and from the third light source to the one or more silicon light detector, are substantially the same; and
wherein the second and fourth light sources are located relative to one another and relative to the one or more silicon light detector so that path lengths from the second light source to the one or more silicon light detector, and from the fourth light source to the one or more silicon light detector, are substantially the same.

3. The implantable system of claim 1, wherein hemoglobin concentration for tissue is determined using the following equation:

$$[H] = \frac{\ln\left(\frac{I(810)}{I_0(810)}\right)}{k_{HbO}^{810} S_{tO2} + k_{Hb}^{810}(1 - S_{tO2})}$$

where
- [H] is the hemoglobin concentration for tissue,
- $k_{HbO}^{810}$ is a known molar absorption coefficient of oxygenated hemoglobin (HbO) for the light having a wavelength of approximately 810 nm,
- $k_{Hb}^{810}$ is a known molar absorption coefficient of deoxygenated hemoglobin (Hb) for the light having a wavelength of approximately 810 nm,
- $S_{tO2}$ is the level of tissue oxygen saturation determined by the system,
- $I_0(810)$ is an initial intensity of the light having a wavelength of approximately 810 nm, and
- $I(810)$ is an intensity of the light having a wavelength of approximately 810 nm as detected by the one or more light detector.

4. The implantable system of claim 3, wherein the system includes an analog to digital converter (A/D) that converts intensities of light detected by the one or more light detector to digital values; and
wherein a value indicative of an initial tissue hydration level is determining using the following equation:

$$W_0 = \frac{\ln(\text{counts}(980)) - \left(k_{HbO}\left(\frac{S_{tO2}}{100}\right) + k_{Hb}\left(1 - \frac{S_{tO2}}{100}\right)\right)[H]}{\mu_{a\_w}^{980}},$$

where
- $W_0$ is the value indicative of the initial tissue hydration level,
- counts(980) is a digital value, provided using the A/D, that is indicative of an intensity of the light of having a wavelength of approximately 980 nm detected by the one or more light detector, and
- $\mu_{a\_w}^{980}$ is the known absorption coefficient of water for the light having a wavelength of approximately 980 nm.

5. The implantable system of claim 4, wherein a value indicative of a change in tissue hydration is determined using the following equation:

$$\Delta W = W_0 - \frac{\ln(\text{counts}(980)) + \left(k_{HbO}\left(\frac{S_{tO2}}{100}\right) + k_{Hb}\left(1 - \frac{S_{tO2}}{100}\right)\right)[H]}{\mu_{a\_w}^{980}},$$

where ΔW is the value indicative of the change in tissue hydration.

6. The implantable system of claim 1, wherein the one or more processor is configured to monitor for pulmonary edema based on the levels of tissue hydration determined by the system.

7. The implantable system of claim 6, further comprising an alert that is triggered when a change in tissue hydration exceeds a corresponding threshold.

8. The implantable system of claim 1, wherein the one or more processor is configured to:
- determine levels of oxygenated hemoglobin (HbO) and deoxygenated hemoglobin (Hb) based on the detected scattered light of the first and third wavelengths; and
- detect and/or track anemia, using detected levels of deoxygenated hemoglobin as a surrogate measure of hematocrit.

9. The implantable system of claim 8, further comprising an alert that is triggered when a change in Hb exceeds a corresponding threshold.

10. An implantable system, comprising:
a plurality of light sources to transmit toward vascularized tissue, in a time multiplexed manner, light having at least two different wavelengths between and inclusive of approximately 610 nm and 910 nm, and light having a wavelength of approximately 980 nm;
one or more silicon light detector to detect light of the at least two different wavelengths between and inclusive of approximately 610 nm and 910 nm, and light having the wavelength of approximately 980 nm, scattered by the vascularized tissue; and
one or more processor configured to detect changes in tissue hydration and changes in at least one of blood oxygen saturation, tissue oxygen saturation and levels of hemoglobin concentration for tissue, based on the scattered light of the at least two different wavelengths between and inclusive of approximately 610 nm and 910 nm, and the scattered light of the wavelength of approximately 980 nm, detected by the one or more silicon light detector.

11. A method for use with an implantable system, comprising:
(a) transmitting toward vascularized tissue, in a time multiplexed manner, light having a first wavelength of approximately 660 nm, light having a second wavelength of approximately 810 nm, light having a third wavelength of approximately 910 nm, and light having a fourth wavelength of approximately 980 nm;
(b) detecting light of the first, second, third and fourth wavelengths scattered by the vascularized tissue using one or more silicon light detector;
(c) determining a level of blood oxygen saturation based on the detected scattered light of the first and third wavelengths;
(d) determining a level of tissue oxygen saturation based on the detected scattered light of the first and third wavelengths;
(e) determining a level of hemoglobin concentration for tissue based on the detected scattered light of the second wavelength; and
(f) determining a level of tissue hydration based on the detected scattered light of the fourth wavelength;
wherein steps (c), (d), (e) and (f) are performed using one or more processor.

12. The method of claim 11, wherein step (e) includes determining a level of hemoglobin concentration for tissue using the following equation:

$$[H] = \frac{\ln\left(\frac{I(810)}{I_0(810)}\right)}{k_{HbO}^{810} S_{tO2} + k_{Hb}^{810}(1 - S_{tO2})}$$

where
- [H] is the hemoglobin concentration for tissue,
- $k_{HbO}^{810}$ is a known molar absorption coefficient of oxygenated hemoglobin (HbO) for the light having a wavelength of approximately 810 nm,
- $k_{Hb}^{810}$ is a known molar absorption coefficient of deoxygenated hemoglobin (Hb) for the light having a wavelength of approximately 810 nm,
- $S_{tO2}$ is the level of tissue oxygen saturation determined by the system, $I_0(810)$ is an initial intensity of the light having a wavelength of approximately 810 nm, and $I(810)$ is an intensity of the light having a wavelength of approximately 810 nm as detected by the one or more light detector.

13. The method of claim 12, wherein step (f) includes:

using an analog to digital converter (A/D) to convert intensities of light detected by the one or more light detector to digital values; and determining a value indicative of an initial tissue hydration level using the following equation:

$$W_0 = \frac{\ln(\text{counts}(980)) - \left(k_{HbO}\left(\frac{S_{tO2}}{100}\right) + k_{Hb}\left(1 - \frac{S_{tO2}}{100}\right)\right)[H]}{\mu_{a\_w}^{980}},$$

where $W_0$ is the value indicative of the initial tissue hydration level, counts(980) is a digital value, provided using the A/D, that is indicative of an intensity of the light of having a wavelength of approximately 980 nm detected by the one or more light detector, and $\mu_{a\_w}^{980}$ is the known absorption coefficient of water for the light having a wavelength of approximately 980 nm.

14. The method of claim 13, wherein step (f) further includes:

determining a value indicative of a change in tissue hydration using the following equation:

$$\Delta W = W_0 - \frac{\ln(\text{counts}(980)) + \left(k_{HbO}\left(\frac{S_{tO2}}{100}\right) + k_{Hb}\left(1 - \frac{S_{tO2}}{100}\right)\right)[H]}{\mu_{a\_w}^{980}},$$

where $\Delta W$ is the value indicative of the change in tissue hydration.

15. The method of claim 11, further comprising monitoring for pulmonary edema based on the levels of tissue hydration determined by the system.

16. The method of claim 15, further comprising triggered an alert when a change in tissue hydration exceeds a corresponding threshold.

17. The method of claim 11, wherein step (c) includes determining levels of oxygenated hemoglobin (HbO) and deoxygenated hemoglobin (Hb) based on the detected scattered light of the first and third wavelengths; and further comprising:

detecting and/or tracking anemia, using detected levels of deoxygenated hemoglobin as a surrogate measure of hematocrit.

18. The method of claim 17, further comprising triggering an alert when a change in Hb exceeds a corresponding threshold.

19. A method for use with an implantable system for monitoring tissue hydration, comprising:

(a) transmitting toward vascularized tissue, in a time multiplexed manner, light having at least two different wavelengths between and inclusive of approximately 610 nm and 910 nm, and light having a wavelength of approximately 980 nm;

(b) using one or more silicon detector to detect light of the at least two different wavelengths between and inclusive of approximately 610 nm and 910 nm, and light having the wavelength of approximately 980 nm, scattered by the vascularized tissue; and (c) detecting changes in tissue hydration and changes in at least one of blood oxygen saturation, tissue oxygen saturation and levels of hemoglobin concentration for tissue, based on the detected scattered light of the at least two different wavelengths between and inclusive of approximately 610 nm and 910 nm, and the scattered light of the wavelength of approximately 980 nm, as detected by the one or more silicon light detector;

wherein step (c) is performed using one or more processor.

* * * * *